(12) United States Patent
Salys et al.

(10) Patent No.: US 7,890,190 B1
(45) Date of Patent: Feb. 15, 2011

(54) DEFLECTABLE HOLLOW STYLET GUIDEWIRE SYSTEM

(75) Inventors: Scott Salys, Los Angeles, CA (US); Ravi Jain, Los Angeles, CA (US)

(73) Assignee: Pacesetter, Inc., Sylmar, CA (US)

( * ) Notice: Subject to any disclaimer, the term of this patent is extended or adjusted under 35 U.S.C. 154(b) by 1031 days.

(21) Appl. No.: 11/677,006

(22) Filed: Feb. 20, 2007

(51) Int. Cl.
*A61N 1/00* (2006.01)
(52) U.S. Cl. .................................. 607/122; 604/164.02
(58) Field of Classification Search .................. 607/120, 607/122, 126–128; 604/164.02
See application file for complete search history.

(56) References Cited

U.S. PATENT DOCUMENTS

| | | | |
|---|---|---|---|
| 5,833,632 A * | 11/1998 | Jacobsen et al. ............ | 600/585 |
| 6,356,791 B1 | 3/2002 | Westlund et al. | |
| 6,456,889 B2 | 9/2002 | Pianca et al. | |
| 6,456,890 B2 | 9/2002 | Pianca et al. | |
| 6,567,704 B2 * | 5/2003 | Sundquist et al. ........... | 607/119 |
| 6,931,286 B2 * | 8/2005 | Sigg et al. .................... | 607/120 |
| 2001/0037136 A1 | 11/2001 | Pianca et al. | |
| 2002/0072737 A1 | 6/2002 | Belden et al. | |
| 2004/0059348 A1 | 3/2004 | Geske et al. | |
| 2005/0070986 A1 | 3/2005 | Tockman et al. | |

* cited by examiner

*Primary Examiner*—Mark W Bockelman

(57) ABSTRACT

A body implantable lead system includes an over-the-wire lead with a longitudinally extending lumen. A hollow stylet having an outer peripheral surface is introduced into the lumen and an annular resilient blood seal within the lumen may be sealingly positioned between the outer peripheral surface of the stylet and the lead to prevent flow of blood beyond the blood seal and into the lumen in a proximal direction. A guidewire is slidably received within the hollow stylet and includes a tip end which may project through the passage at the distal end of the lead such that relative movement of the guidewire and stylet within the lead is enabled while avoiding friction between the blood seal and the guidewire. Either the guidewire or the stylet may be pre-shaped for proper placement of the lead for engagement with the body tissue and surrounded by a semi-rigid retractable sheath.

6 Claims, 4 Drawing Sheets

DEFLECTABLE HOLLOW STYLET GUIDEWIRE SYSTEM

TECHNICAL FIELD

The present invention generally relates to the implantation of stimulation leads for use with implantable cardiac stimulation devices. The present invention more particularly relates to a simplified technique of lead delivery resulting in reduced tool exchanges and reduced friction in blood seal equipped leads or catheters

BACKGROUND

Implantable cardiac stimulation devices are well known in the art. Such devices may include, for example, pacemakers or defibrillators. These devices are generally implanted in an upper portion of the chest beneath the skin of a patient within what is known as a subcutaneous pocket.

Traditionally, therapy delivery has been limited to the right side of the heart. To that end, one or more stimulation leads are implanted within the heart. The leads may include one or more electrodes positioned within the right ventricle or right atrium, or both, of the heart for making electrical contact with their respective heart chambers. Conductors within the leads couple the electrodes to the device to enable the device to deliver the desired cardiac stimulation therapy.

More recently, cardiac stimulation leads and methods have been proposed and even practiced for delivering cardiac stimulation therapy from or to the left side of the heart. These lead structures and methods involve lead implantation within the coronary sinus and/or the great vein of the heart and/or coronary sinus veins, for example, since the coronary sinus is closely adjacent the left atrium and extends into the great vein which is adjacent the left ventricle of the heart. Electrodes thus placed in the coronary sinus and great vein may be used for various forms of cardiac stimulation therapy such as left atrial pacing, left ventricular pacing, and even cardioversion and defibrillation, for example.

Cardiac stimulation lead placement within the left side of the heart can require lead placement in difficult-to-reach veins and arteries. Typically, an outer support sheath is used to cannulate or access the coronary sinus. This sheath or a separate sheath may be then used to access a branch vessel of the coronary sinus (i.e. subselect a vessel). Once the lead is inserted into the coronary sinus or branch vessel, either a solid stylet wire or guidewire is used to advance and guide the lead to its final desired position for optimal clinical performance.

The use of the methods described above present several issues described below:

(a) Use or exchange of outer support sheaths for cannulation and branch vessel selection may result in complications such as lead dislodgement, blood vessel dissection, and prolonged surgery time.

(b) Cardiac stimulation leads are currently designed to use either a stylet or guidewire, but not both concurrently. This requires that a physician exchange one tool for the other in order to navigate tortuous anatomy to the desired final position.

(c) Once the lead is placed, the outer support sheath must be slit or peeled away from the pacing lead in order to remove it from the patient's body since the proximal portion of the lead such as the connector boot and connector seals are typically larger in diameter than the sheath diameter. The need to slit or peel the external sheath increases the surgical procedure time, surgical procedure cost, and probability of surgical complications.

(d) During the procedure, leads designed to allow intraluminal passage of guidewires or stylets also allow blood to flow through the lead and out of the body, clogging the lead lumen and making surgery more difficult. Current lumen seals are undesirable because the friction between the seal and the guidewire or stylet reduces tactile feedback to the implanting physician when advancing the lead, stylet, or guidewire.

The present invention provides an elegant solution to the aforementioned problems, permitting the concomitant use of both a stylet and a guidewire for implanting a stimulation lead with the additional benefits of intraluminal deflection of the lead and opening of the blood seal. Not only is a lead so adaptable, the adaptation may be easily made, requires minimal components, and may be accomplished with tools already made available to the surgeon.

It was in light of the foregoing known apparatus and techniques that the present invention was conceived and has now been reduced to practice.

SUMMARY OF THE INVENTION

A stimulation lead system for positioning the lead of a body implantable stimulating pulse generator adapted to transmit electrical signals between proximal and distal end portions to thereby stimulate selected body tissue includes an over-the-wire lead having a lumen extending between an end surface at a distal end and a proximal end and having a passage extending between the end surface and the lumen. A hollow stylet is introduced into the lumen and an annular resilient blood seal is sealingly positioned between the outer peripheral surface of the stylet and the lead to prevent flow of blood into the lumen of the lead in a proximal direction. A guidewire slidably received within the hollow stylet includes a tip end projecting through the passage at the distal end of the lead enabling relative movement of the guidewire and the stylet within the lead while avoiding friction between the blood seal and the guidewire.

According to the invention, a hollow stylet is employed that opens the blood seal in an OTW lead and allows simultaneous passing of a guidewire through the hollow stylet and the OTW lead. The hollow stylet may be deflectable to allow better positioning of the guidewire and OTW lead without the need to exchange various sheaths.

In the preferred embodiment of this invention, a hollow tube is used as the stylet for OTW lead placement. This design allows the hollow stylet to open a blood seal placed in the distal region of the OTW lead while providing a central lumen for simultaneous guidewire passage.

An added benefit of this design is that the hollow stylet may be preshaped to allow for deflection of the OTW lead and/or the guidewire for better OTW lead placement. As an added feature, a preshaped guidewire or shapeable core wire may be used in conjunction with the straight or preshaped hollow stylet to gain a deflection of the lead or catheter when the hollow stylet is retracted. For explanation of the terminology being used, a guidewire is a specific tool with specific design features that is placed in the venous anatomy and used as the track over which the lead is advanced. A core wire would be a generic wire inserted into the hollow stylet. The core wire would not be used to advance the lead, but only to direct the lead. It would not protrude from the lead tip. If both a preshaped hollow stylet and shapeable core wire are used, a compound deflection of the lead or catheter may be induced.

For purposes of the ensuing description, however, the term guidewire shall be used exclusively to refer to both a guidewire and a core wire since, in effect, a core wire is only a more robust guidewire but generally operates in the same manner. Of course, being more robust, the core wire can be preshaped while a conventional guidewire would be too weak or fragile to provide guidance for the lead.

In one alternate embodiment of this invention, the preshaped hollow stylet is surrounded by a semi-rigid, retractable sheath to allow physicians to control the angle of stylet deflection.

A primary feature of the invention, then, is the provision of a novel technique for implanting cardiac stimulation leads for use with implantable cardiac stimulation devices.

Another feature of the present invention is the provision of such a simplified technique of lead delivery resulting in reduced tool exchanges.

Still another feature of the present invention is the provision of such a technique which enables simultaneous passage of a guidewire and stylet through an over-the-wire style lead.

Yet another feature of the present invention is the provision of such a technique which eliminates the need for an external support sheath around the lead during its placement.

Yet a further feature of the present invention is the provision of such a technique for which a robust OTW lead deflection mechanism includes a preformed hollow tube surrounded by a retractable sheath.

Still another feature of the present invention is the provision of such a technique which eliminates friction between the blood seal and guidewire.

Yet another feature of the present invention is the provision of such a technique which enables use of a shapeable or deflectable hollow stylet to deflect the OTW lead for placement.

Still a further feature of the present invention is the provision of such a technique for which a retractable sheath can be retracted resulting in deflection of the lead.

Yet another feature of the present invention is the provision of such a technique which permits rapid insertion and exchange of a deflection device into the lead without requiring use of an external device such as a sheath around the lead or destruction of the deflection device.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and together with the description, serve to explain the principles of the invention in general terms. Like numerals refer to like parts throughout the disclosure.

DETAILED DESCRIPTION OF THE PREFERRED EMBODIMENTS

Figure 1:
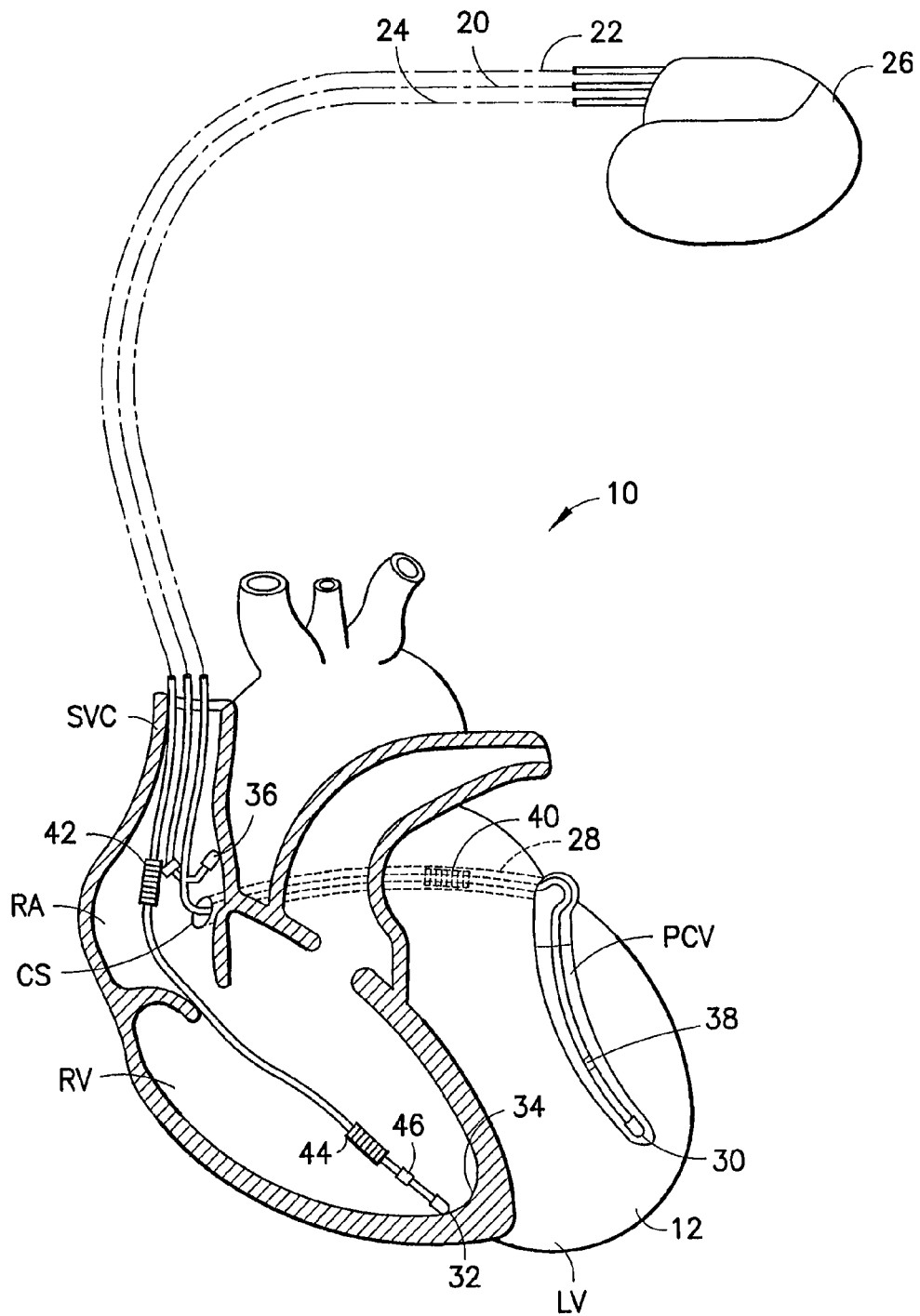
FIG. 1 is a diagrammatic perspective view illustrating an implanted lead system for providing electrical stimulation of a heart, the lead system being of the type which can be implanted using the techniques of the present invention.

Refer now to the drawings and, initially, to FIG. 1 in which is shown a diagrammatic perspective view of an implanted system 10 for providing electrical stimulation of a heart 12 incorporating features of the present invention. Although the present invention will be described with reference to the embodiments shown in the drawings, it should be understood that the present invention can be embodied in many alternate forms or embodiments. In addition, any suitable size, shape or type of elements or materials could be used.

In FIG. 1, implantable leads 20, 22, 24 are illustrated generally embodying apparatus for stimulation of the body, the heart 12 in this instance, by means of a pacemaker 26 or other suitable pulse generating or stimulating device. This is a diagrammatic cross section view of a human heart showing the right atrium RA and the right ventricle RV along with the coronary sinus CS and a vein 28 of the left side of the heart. This vein of the left side could be any of the veins found on the left side of the heart such as the great cardiac vein, posterior vein, or the lateral vein of the left ventricle LV. The leads are shown in a typical placement, lead 20 being an RA lead, lead 22 being an RV lead, and lead 24 being an LV lead inserted via the superior vena cava SVC into the coronary sinus ostium CSO located in the right atrium RA. The lead 24 is then advanced through the coronary sinus ostium, passing through the coronary sinus CS and placed into a tributary of the coronary venous system, preferably the left posterior cardiac vein PCV with an associated tip electrode 30 being placed deep in the distal portion of the left side of the heart.

The phrase "coronary venous system" refers to the coronary sinus vein, great cardiac vein, left marginal vein, left posterior vein, middle cardiac vein, and/or small cardiac veins or any other cardiac vein accessible by the coronary sinus. From this location, the lead 24 can be used to stimulate the left ventricle LV. Clearly, the lead 24 must follow a tortuous path in order for the tip electrode 30 to reach its intended destination. The lead 22 extends to a tip electrode 32 placed in the apex 34 of the right ventricle RV and illustrates the typical position of a lead in the right ventricle. The lead 20 extends to a tip electrode 36 shown in the appendage of the right atrium RA and illustrates the typical position of the lead in the appendage of the right atrium. In this scenario, component 38 is typical of a proximal ring electrode of the LV lead 24, component 40 is typical of a shock electrode of the LV lead 24, component 42 is typical of a proximal shock coil of the RV lead 22, component 44 is typical of a distal shock coil of the RV lead 22, and component 46 is typical of a ring electrode of the RV lead 22.

It was earlier explained that as a result of recent advancements in techniques and instrumentation, many physicians have become convinced that a lead that is placed with a guidewire, instead of a stylet, is superior. However, more often than not, an implanter may choose to use a combination of a stylet and guidewire in the placement of an LV lead. One thrust of the present invention, therefore, is to mitigate the switching out of the stylet and/or guidewire, employed in the implant of a LV lead.

Figure 2:
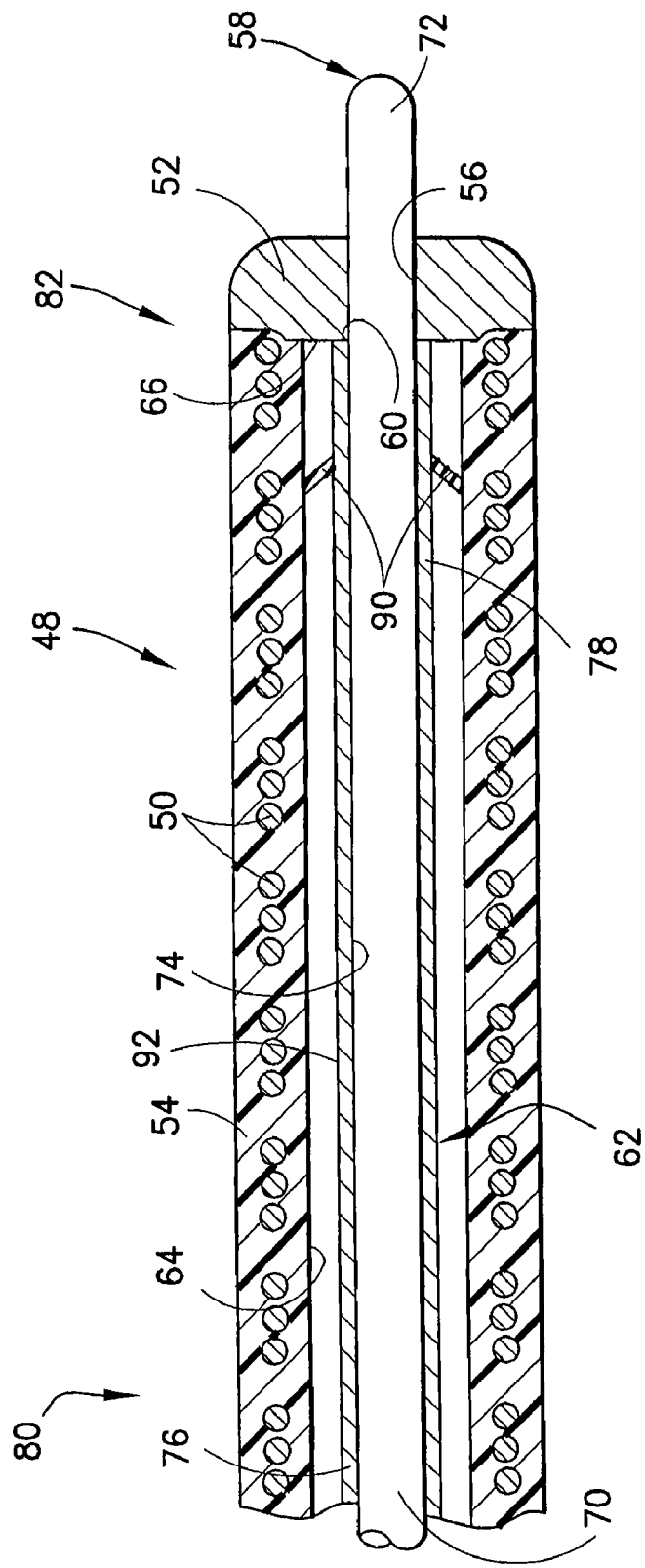
FIG. 2 is a detail longitudinal cross sectional view of the distal end of a lead system employing a combination of guidewire and hollow stylet, according to the invention, for the implanting operation.

Leads that are used with guidewires to gain access to the coronary venous system must have an open lumen at the distal tip of the lead to allow the guidewire to pass through. In this regard, turn now to FIG. 2. Here, a stimulating lead 48 is illustrated as including a coil conductor 50 coupled to a distal electrode 52, the conductor shown embedded in an insulating sheath 54 of suitable flexible, resilient, insulative material, typically, polyurethane, silicone, or other suitable polymeric material. However, it will be understood that the conductor 50 may also be freely received in a lumen of insulating sheath 54 should that be desired. The distal electrode 52 has an aperture 56 for reception therethrough of a guidewire 58 for use in implanting the lead. The metallic components may be stainless steel, MP35N, Nitonol, or a metallic polymer, for example. However, when an implanting physician finds that the guidewire method is not successful, it is possible using the construction of the present invention to instead make use of a hollow stylet 62.

To this end, a distal tip end 60 of the stylet 62 passes through a lumen 64 of the lead and stops at a proximally facing bearing surface or thrusting region 66.

According to the preferred technique of the invention, the guidewire 58 extending between proximal and distal ends 70, 72, respectively, is introduced into a longitudinally extending internal passage 74 of the hollow stylet 62, itself extending between proximal and distal ends 76, 78, respectively. Thereupon, the combination of the stylet 62 and guidewire 58 are introduced into the longitudinally extending lumen 64 of the lead 48 which also extends between proximal and distal ends 80, 82, respectively. With the distal tip end 60 of the stylet 62 in engagement with the bearing surface or thrusting region 66 of the distal electrode 52, the stylet together with the lead and guidewire are advanced until such time that the lead encounters a tortuous turn in the vasculature of the body.

If or when that occurs, the guidewire 58 is advanced through the stylet 62 and into the vasculature until the distal end 72 of the guidewire 58 arrives at a chosen location. At this point, with the guidewire 58 bridging the tortuous turn in the vasculature of the body, once again, the stylet proceeds and continues to advance together with the lead 48 since the distal tip end 60 is engaged with the bearing surface 66. Such advance continues until the lead 48 reaches the desired implant location. When the desired implant location is reached, additional force is desirably imparted to the stylet 62 acting against the thrusting region 66 of the distal electrode 52 to wedge the distal end 82 of the lead 48 into place at the desired implant location.

Thereafter, the guidewire 58 is withdrawn from the vasculature and likewise the stylet. One of the primary benefits of the invention, then, is that it permits simultaneous usage of both the stylet and guidewire while eliminating the need to interchange between those two components in order to achieve optimal anatomical placement of the lead.

Figure 3:
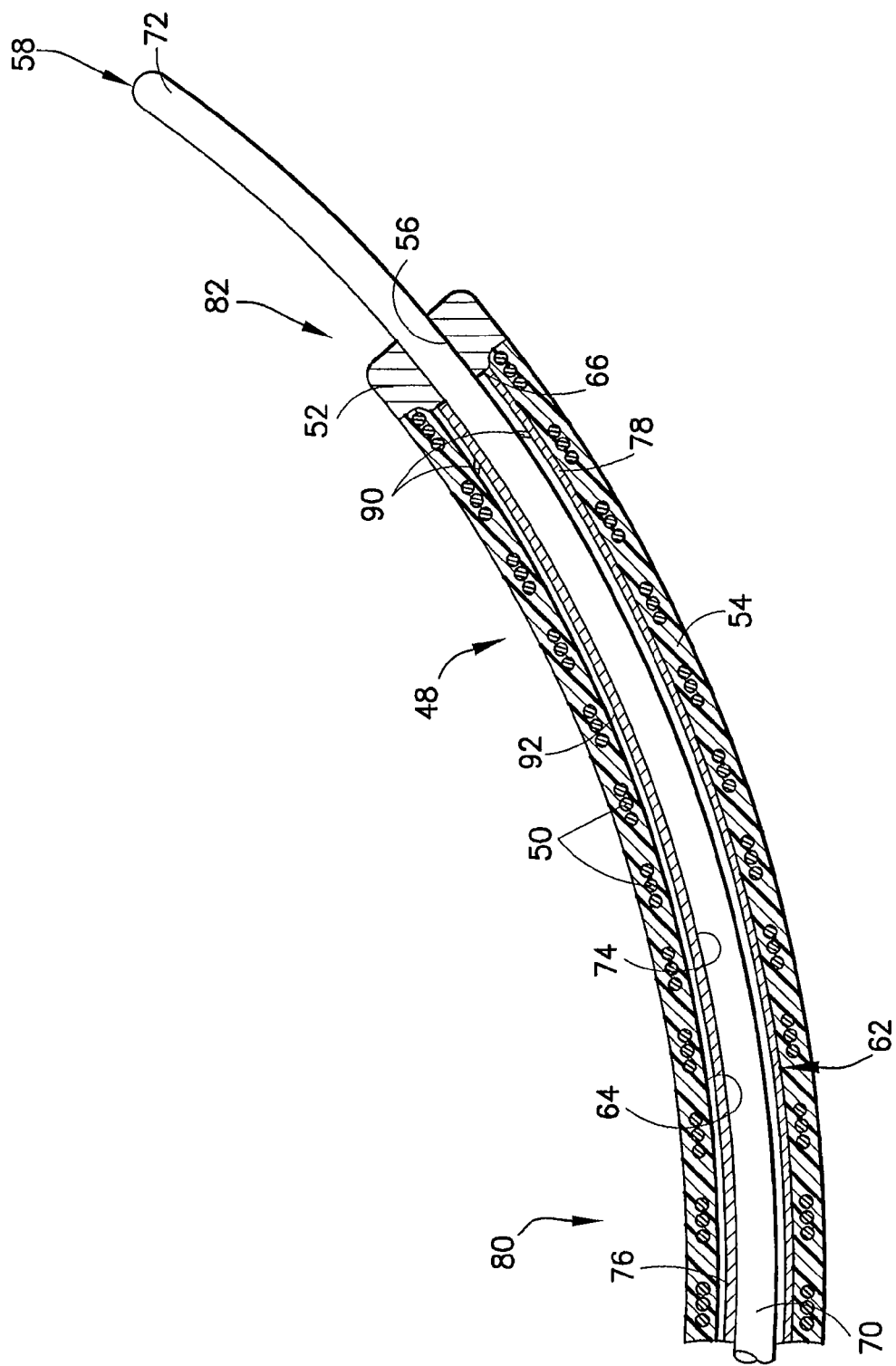
FIG. 3 is a detail longitudinal cross sectional view of the distal end of the lead system illustrating one or more of the components of the of the catheter, hollow stylet, and guidewire being preshaped to aid in proper placement of the guidewire for its engagement with the body tissue.
Figure 4:
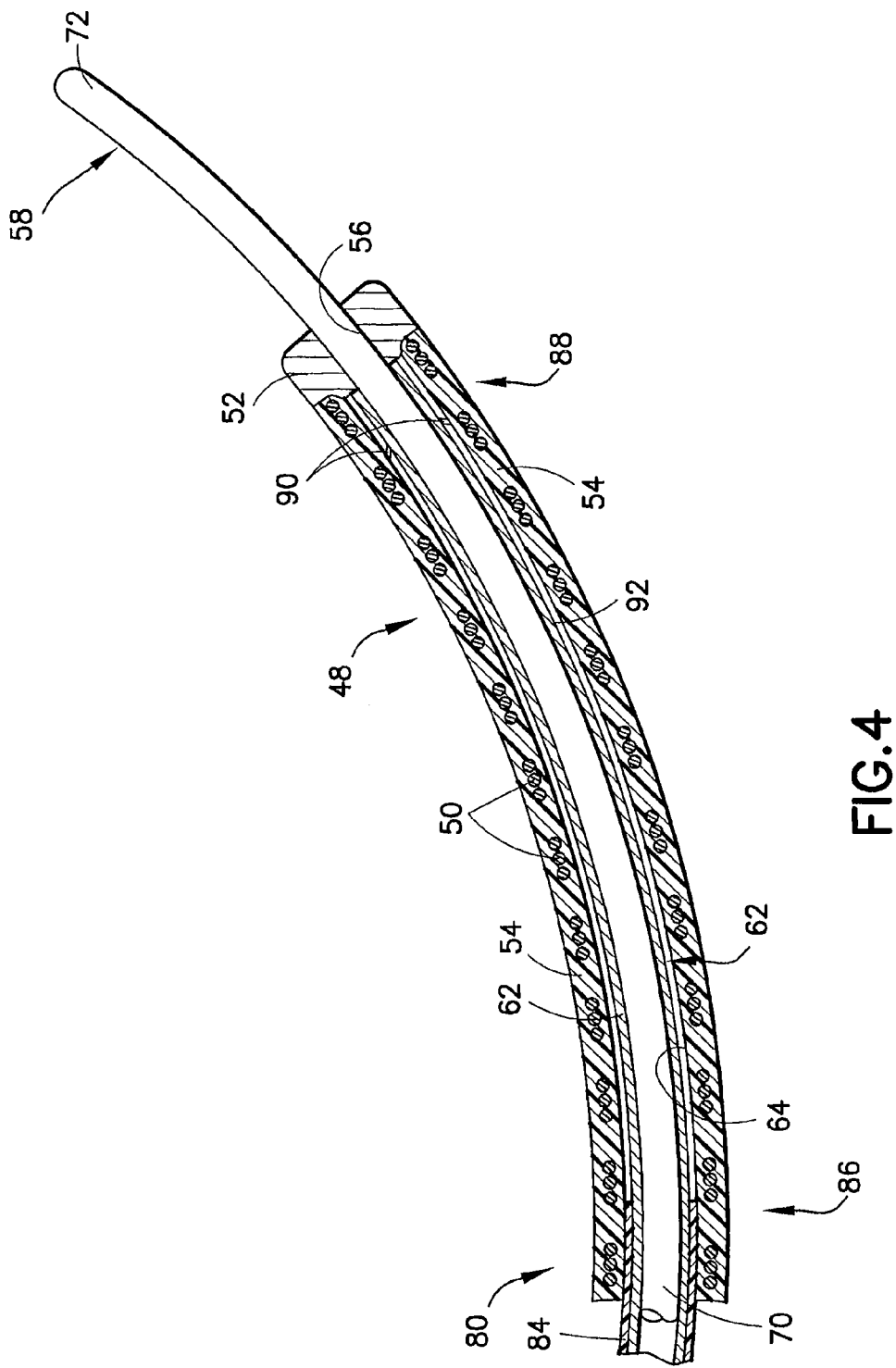
FIG. 4 is another detail longitudinal cross sectional view of the distal end of a lead system, similar to FIG. 3 illustrating a flexible retractable guide sheath slidably introduced into catheter to straighten the catheter, as desired.

For this procedure, and specifically viewing FIG. 3, either one of the hollow stylet 62 and the guidewire 58 may be preshaped in a known manner to aid in the proper placement of the guidewire for its engagement with the body tissue at the location being sought. Retraction or insertion of an appropriate one of these components results in the desired deflection of the distal end of the lead. To further aid in the proper placement of the guidewire, viewing FIG. 4, a flexible retractable sheath 84 may be slidably introduced into the lumen 64 between the lead 48 and the hollow stylet 62 distant from the distal end of the lead. The retractable sheath 84 can be moved between a proximal location 86, as illustrated, and a distal location 88 in the lumen 64 to thereby straighten the lead, stylet, and guidewire and thereby aid in the desired placement of the tip end of the guidewire for engagement with the body tissue at the location being sought. One of the primary benefits of this invention is the ability to deflect the hollow stylet 62 to aid subselection or cannulation of the coronary sinus at the beginning of the procedure.

A further important component of the invention is the employment of an annular resilient blood seal 90 within the lumen 64 sealingly positioned between an outer peripheral surface 92 of the stylet and the inner peripheral surface of the lumen 64 of the lead to prevent flow of blood beyond the blood seal and into the lumen in a proximal direction. The blood seal may be composed of a flexible polymeric material such as polyurethane or silicone. The blood seal 90 may be fixed to the lead at its distal end, sealingly engaging the outer peripheral surface of the stylet. In this instance, the distal tip end 60 of the hollow stylet 62 is used to open the seal as the stylet is advanced into engagement with the bearing surface 66. This construction allows precise feedback to the attending physician from the guidewire without any drag from the blood seal.

While preferred embodiments of the invention have been disclosed in detail, it should be understood by those skilled in the art that various other modifications may be made to the illustrated embodiments without departing from the scope of the invention as described in the specification and defined in the appended claims.

What is claimed is:

1. A body implantable stimulation lead system for positioning the lead of a body implantable stimulating pulse generator comprising:
   an over-the-wire lead extending between an end surface at a distal end and a proximal end and having a lumen therein and having a passage extending between the end surface and the lumen;
   a hollow stylet having an outer peripheral surface introduced into the lumen of the lead and extending between the distal and proximal ends thereof;
   an annular resilient blood seal within the lumen sealingly positioned between the outer peripheral surface of the stylet and the lead to prevent flow of blood beyond the blood seal and into the lumen in a proximal direction, wherein the blood seal is fixed to the outer peripheral surface of the stylet and sealingly engages the lead at the distal end thereof; and
   a guidewire slidably received within the hollow stylet and including a tip end projectable through the passage at the distal end of the lead;
   whereby relative movement of the guidewire and the stylet within the lead is enabled while avoiding friction between the blood seal and the guidewire.

2. A body implantable stimulation lead system as set forth in claim 1
   wherein the lead is preshaped for deflecting the tip end of the guidewire to aid in its proper placement for engagement with the body tissue at the location being sought.

3. A body implantable stimulation lead system as set forth in claim 1
   wherein the hollow stylet is preshaped for deflecting the tip end of the guidewire to aid in its proper placement for engagement with the body tissue at the location being sought.

4. A body implantable stimulation lead system as set forth in claim 1
   wherein the guidewire is preshaped for deflecting its tip end to aid in the proper placement thereof for engagement with the body tissue at the location being sought.

5. A body implantable stimulation lead system as set forth in claim 1
wherein the blood seal is fixed to the lead at the distal end thereof and sealingly engages the outer peripheral surface of the stylet.

6. A body implantable stimulation lead system for positioning the lead of a body implantable stimulating pulse generator comprising:
an over-the-wire lead extending between an end surface at a distal end and a proximal end and having a lumen therein and having a passage extending between the end surface and the lumen;
a hollow stylet having an outer peripheral surface introduced into the lumen of the lead and extending between the distal and proximal ends thereof;
an annular resilient blood seal within the lumen sealingly positioned between the outer peripheral surface of the stylet and the lead to prevent flow of blood beyond the blood seal and into the lumen in a proximal direction; and
a guidewire slidably received within the hollow stylet and including a tip end projectable through the passage at the distal end of the lead;
whereby relative movement of the guidewire and the stylet within the lead is enabled while avoiding friction between the blood seal and the guidewire,
wherein one of the hollow stylet and the guidewire is preshaped to aid in the proper placement of the lead for its engagement with the body tissue at the location being sought; and including:
a flexible retractable sheath slidably received in the lumen between the lead and the hollow stylet and movable between a proximal location and a distal location to thereby straighten the lead, hollow stylet, and/or guidewire and thereby aid in the desired placement of the tip end of the guidewire for engagement with the body tissue at the location being sought.

* * * * *